(12) United States Patent
Brede

(10) Patent No.: US 9,386,755 B2
(45) Date of Patent: Jul. 12, 2016

(54) TURFGRASS VARIETIES HAVING DESIRABLE LOOKING TURF WHEN MOWED INFREQUENTLY

(71) Applicant: J.R. SIMPLOT COMPANY, Boise, ID (US)

(72) Inventor: Andrew Douglas Brede, Veradale, WA (US)

(73) Assignee: J.R. SIMPLOT COMPANY, Boise, ID (US)

( * ) Notice: Subject to any disclaimer, the term of this patent is extended or adjusted under 35 U.S.C. 154(b) by 0 days.

(21) Appl. No.: 14/206,535

(22) Filed: Mar. 12, 2014

(65) Prior Publication Data

US 2015/0373941 A1   Dec. 31, 2015

Related U.S. Application Data

(60) Provisional application No. 61/782,611, filed on Mar. 14, 2013.

(51) Int. Cl.
| | |
|---|---|
| A01H 5/10 | (2006.01) |
| A01H 5/12 | (2006.01) |
| A01G 1/00 | (2006.01) |
| A01H 1/02 | (2006.01) |
| C12N 15/82 | (2006.01) |

(52) U.S. Cl.
CPC *A01H 5/12* (2013.01); *A01G 1/005* (2013.01); *A01H 1/02* (2013.01); *C12N 15/8241* (2013.01); *C12N 15/8274* (2013.01); *C12N 15/8275* (2013.01); *C12N 15/8277* (2013.01); *C12N 15/8278* (2013.01); *C12N 15/8279* (2013.01); *C12N 15/8286* (2013.01)

(58) Field of Classification Search
None
See application file for complete search history.

(56) References Cited

U.S. PATENT DOCUMENTS

| | | | |
|---|---|---|---|
| 5,523,520 A | 6/1996 | Hunsperger et al. | |
| PP18,934 P2 * | 6/2008 | Hardison et al. | A01H 5/00 Plt./393 |
| PP21,045 P2 * | 6/2010 | Burr | A01H 5/00 Plt./393 |
| 2006/0031969 A1 * | 2/2006 | Hardison | A01H 5/12 800/320 |
| 2007/0074303 A1 * | 3/2007 | McCutchen | C12N 9/1092 800/278 |
| 2009/0070896 A1 * | 3/2009 | Horita | C12N 15/8286 800/279 |
| 2016/0029585 A1 | 2/2016 | Brede | |

OTHER PUBLICATIONS

Bigelow et al, 2003, Kentucky Bluegrass Lawn Turf Response to Three Autumn Applied Urea Sources, p. 75-78.*
Fan et al, 2009, Front. Agric. China, 3:186-189.*
Anderson et al, 1994, Grass Varieties in the United States, U.S. Dept. of Agriculture, Handbook No. 170:1-296.*
Zhang et al, 2010, Plant Cell Tiss Organ Cult, 102:135-143.*
Brilman, 2013, SportsTurf, 12-15.*
Eshed, et al., 1996, Less-than-additive epistatic interactions of quantitative trait loci in tomato, Genetics, 143:1807-1817.
Kraft, et al., 2000, Linkage disequilibrium and fingerprinting in sugar beet, Theor. Appl. Genet., 101:323-326.
Brede, D., 2000, Turfgrass Maintenance Reduction Handbook: Sports, Lawns, and Golf, Ann Arbor Press, Chelsea, MI, p. 93.
U.S. Appl. No. 15/097,156, filed Apr. 12, 2016, J.R. Simplot Company.
Bigelow, et. al., Kentucky bluegrass lawn turf response to three autumn applied urea sources, 2003, p. 75-78.
Fan, et. al., Growth responses of Kentucky bluegrass (*Poa pratensis* L.) to trinexapac-ethyl applied in spring and autumn, Front. Agric. China, 2009, 3(2):186-189.

* cited by examiner

*Primary Examiner* — Jason Deveau Rosen
(74) *Attorney, Agent, or Firm* — Jondle & Associates, P.C.

(57) ABSTRACT

Turfgrass varieties with desirable looking turf when mowed infrequently are provided. Also provided is a method of producing a turfgrass plant having desirable looking turf when mowed infrequently. The turfgrass plants of the present invention display green leaf chlorophyll concentrations above 1.8 mg/g and a field insitu CM-1000 chlorophyll meter reading of 341.7 or higher, as well as high general turfgrass quality ratings. The turfgrass plants of the present invention retain a dark green color even when scalped back by infrequent mowing.

5 Claims, 1 Drawing Sheet

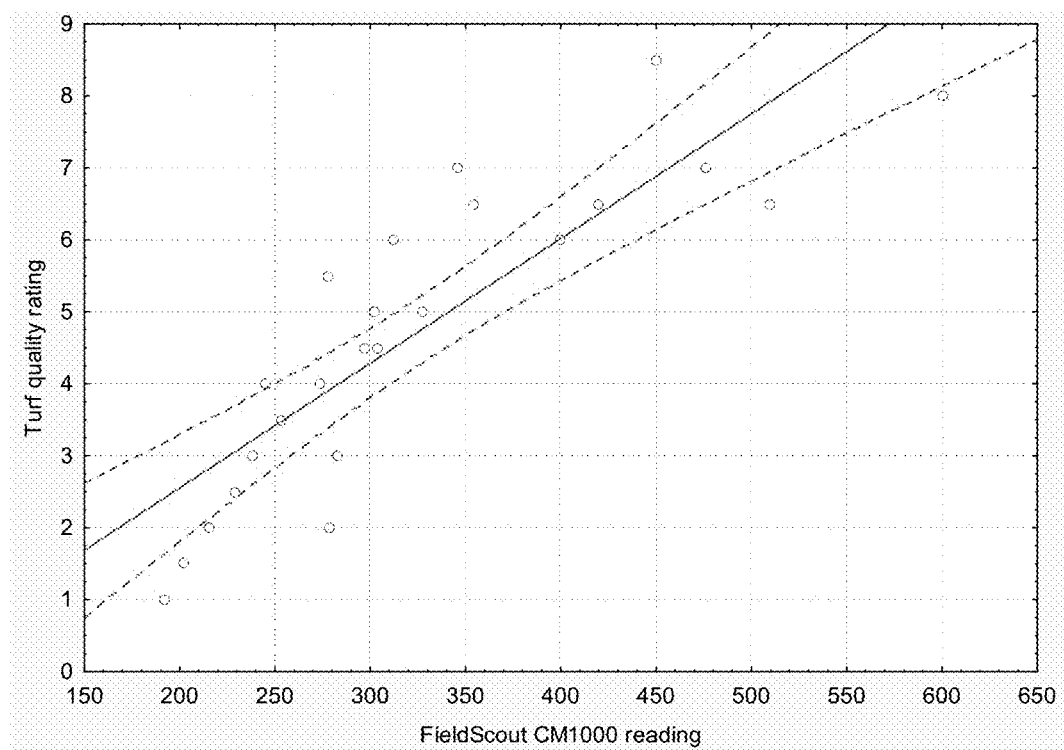

TURFGRASS VARIETIES HAVING DESIRABLE LOOKING TURF WHEN MOWED INFREQUENTLY

CROSS REFERENCE TO RELATED APPLICATIONS

This application claims the benefit of priority from U.S. provisional patent application Ser. No. 61/782,611, filed on Mar. 14, 2013, which is incorporated herein by reference in its entirety.

BACKGROUND OF THE INVENTION

The present invention relates to turfgrass varieties having desirable looking turf when mowed infrequently. All publications cited in this application are herein incorporated by reference.

Turfgrass plays a major role in our daily life. Turfgrass, from a beautification standpoint, provides a canvas for landscaped areas contributing to aesthetic appeal and adding to economic value. Recreational facilities include an array of sports fields, golf courses, parks and lawns. Turfgrass also provides functional value including dust control, erosion control, and glare reduction.

Use and appearance are prime considerations for turfgrass. To best serve a particular function, the turf should be suitable for the use for which it is intended and aesthetically appealing. It should also be well-adapted to the environment where it will be planted. Based on climatic adaptation, turfgrass species have been placed into four categories: adapted for cool humid regions, warm humid regions, cool arid regions, and warm arid regions. The major turfgrasses adapted to the cool humid regions, and irrigated areas of the cool arid regions, are species of *Agrostis, Poa, Festuca*, and *Lolium*. In the warm humid and irrigated areas of the warm arid regions, the major adapted turfgrasses are species of *Cynodon, Zoysia, Stenotaphrum, Eremochloa, Paspalum, Festuca*, and *Agropyron*. In the non-irrigated warm arid regions, species of *Buchloe* and *Bouteloua* are adapted.

Kentucky bluegrass (*Poa pratensis*), also called smooth meadow grass, spear grass and June grass, is a perennial species of grass native to Europe, northern Asia and the mountains of Algeria and Morocco. Although the species is spread over all of the cool, humid parts of the United States, Kentucky bluegrass is native only to portions of North America. Kentucky bluegrass forms a valuable pasture plant, characteristic of well-drained, fertile soil, and is a popular sod-forming grass that is used on golf courses, ski slopes, campsites, gardens and lawns. Kentucky bluegrass is also an important forage species for sheep and cattle. The name Kentucky bluegrass derives from its flower heads, which are blue when the plant is allowed to grow to its natural height of two to three feet.

Over 100 varieties of Kentucky bluegrass have been developed during the past 25 years. Some varieties tolerate southern climates better than others, some have moderate shade tolerance, and some tolerate closer mowing. Many of these grasses also differ in their degree of susceptibility to diseases. Kentucky bluegrass is distinguished from Canada bluegrass (*Poa compressus*) by its darker green foliage, longer leaves, and pubescence at the bases of the leaves. Kentucky bluegrass can also be compared to Annual Meadowgrass (*Poa annua*) and Rough Meadowgrass (*Poa trivialis*), which have a ligule that is silvery and pointed, whereas Kentucky bluegrass has a ligule that is extremely short and square ended.

Kentucky bluegrass is often included in seed mixes that are used to revegetate roadbanks Kentucky bluegrass is a slow-growing plant that establishes in 2 to 3 years and forms a dense sod. Kentucky bluegrass grows best on well-drained loams or clay loams rich in humus and on soils with limestone parent material. Kentucky bluegrass needs large amounts of nitrogen during active growth stages and has an optimal soil pH of between 5.8 and 8.2. Additionally, Kentucky bluegrass is intolerant of drought, excessive flooding high water tables, and poorly drained soils, and is sometimes vulnerable to fungal infections including *Fusarium, Helminthosporium*, leaf spot, rust and powdery mildew.

Kentucky bluegrass typically grows 18 to 24 inches tall and is readily identified by its boat-shaped leaf tip. Kentucky bluegrass spreads by rhizomes and tillers and forms a dense sod. New shoots (rhizomes and tillers) are produced primarily in the spring and late summer. Most shoots produced in the spring remain vegetative, while shoots produced in late summer often terminate in an inflorescence the following spring. The lifetime of a Kentucky bluegrass shoot that terminates in an inflorescence ends soon after the seeds mature.

Because use and appearance are prime considerations for turfgrass, it is desirable to have turfgrass varieties that can be less frequently mowed (defoliated) and still produce an attractive, green lawn turf.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

In one aspect of the present invention there is provided a method of producing a turfgrass plant having desirable looking turf when mowed infrequently.

In one aspect of the invention there are provided turfgrass varieties that produce a desirable looking turf when mowed infrequently, such as mowed once every 4 weeks or more.

In one aspect of the present invention there are provided turfgrass varieties that have chlorophyll concentrations above 1.8 mg/g.

In one aspect of the present invention there are provided turfgrass varieties that have a CM-1000™ field chlorophyll reading of 341.7 or higher resulting in a darker green color and less brown when mowed.

In another aspect of the present invention there are provided turfgrass varieties that have low-growing characteristics.

In another aspect of the present invention there are provided turfgrass varieties that have high general turfgrass quality ratings.

In a further aspect of the present invention there are provided Kentucky bluegrass plants of varieties '03-0582', '03-0441', and '99-2495'. Also provided are seeds and progeny of these varieties.

According to the invention, there are provided novel turfgrass varieties having desirable looking turf when mowed infrequently, including Kentucky bluegrass varieties designated '03-0582', '03-0441', and '99-2495'. This invention thus relates to the seeds of novel turfgrass varieties, such as '03-0582', '03-0441', and '99-2495', to the plants or part(s)

thereof of novel turfgrass varieties, such as Kentucky bluegrass varieties '03-0582', '03-0441', and '99-2495', to plants or part(s) thereof having all the phenotypic and morphological characteristics of novel turfgrass varieties, such as Kentucky bluegrass varieties '03-0582', '03-0441', and '99-2495'. Plant parts of the Kentucky bluegrass varieties of the present invention are also provided.

In another aspect, the present invention provides regenerable cells for use in tissue culture of turfgrass varieties having desirable looking turf when mowed infrequently, including Kentucky bluegrass varieties '03-0582', '03-0441', and '99-2495'. The tissue culture will preferably be capable of regenerating plants having the physiological and morphological characteristics of the turfgrass of the present invention, such as Kentucky bluegrass varieties '03-0582', '03-0441', and '99-2495'. Preferably, the cells of such tissue culture will be embryos, meristematic cells, seeds, callus, pollen, leaves, anthers, pistils, roots, root tips, pods, flowers and stems. Protoplasts produced from such tissue culture are also included in the present invention. The turfgrass plants regenerated from the tissue culture are also part of the invention.

Also included in the invention are methods for producing a turfgrass plant produced by crossing turfgrass varieties having desirable looking turf when mowed infrequently, such as Kentucky bluegrass variety '03-0582', '03-0441', or '99-2495' with itself or another turfgrass or Kentucky bluegrass variety. When crossed with itself, i.e., when crossed with another Kentucky bluegrass variety '03-0582', '03-0441', or '99-2495' plant or self-pollinated, Kentucky bluegrass variety '03-0582', '03-0441', or '99-2495' will be conserved. When crossed with another, different bluegrass plant, an $F_1$ hybrid seed is produced. $F_1$ hybrid seeds and plants produced by growing said hybrid seeds are included in the present invention. A method for producing an $F_1$ hybrid seed comprising crossing a turfgrass plant of the present invention having desirable looking turf when mowed infrequently, such as Kentucky bluegrass variety '03-0582', '03-0441', or '99-2495' plant with a different bluegrass plant and harvesting the resultant hybrid bluegrass seed are also part of the invention. The hybrid bluegrass seed produced by the method comprising crossing a turfgrass plant having desirable looking turf when mowed infrequently, such as Kentucky bluegrass variety '03-0582', '03-0441', or '99-2495' plant with a different bluegrass plant and harvesting the resultant hybrid bluegrass seed, are included in the invention, as are the hybrid bluegrass plant or part(s) thereof, and seeds produced by growing said hybrid bluegrass seed.

In another aspect, the present invention provides transformed turfgrass varieties having desirable looking turf when mowed infrequently, including '03-0582', '03-0441', or '99-2495' Kentucky bluegrass variety plants or part(s) thereof that have been transformed so that its genetic material contains one or more transgenes, preferably operably linked to one or more regulatory elements. Also, the invention provides methods for producing a turfgrass plant having desirable looking turf when mowed infrequently containing in its genetic material one or more transgenes, preferably operably linked to one or more regulatory elements, by crossing transformed turfgrass plants, such as '03-0582', '03-0441', or '99-2495' Kentucky bluegrass variety plants with either a second plant of another turfgrass or bluegrass variety, or a non-transformed '03-0582', '03-0441', or '99-2495' Kentucky bluegrass variety, so that the genetic material of the progeny that results from the cross contains the transgene(s), preferably operably linked to one or more regulatory elements. The invention also provides methods for producing a turfgrass plant having desirable looking turf when mowed infrequently that contains in its genetic material one or more transgene(s), wherein the method comprises crossing the turfgrass variety, such as '03-0582', '03-0441', or '99-2495' with a second turfgrass or bluegrass variety of another bluegrass variety which contains one or more transgene(s) operably linked to one or more regulatory element(s) so that the genetic material of the progeny that results from the cross contains the transgene(s) operably linked to one or more regulatory element(s). Transgenic turfgrass cultivars, or part(s) thereof produced by the methods are in the scope of the present invention.

More specifically, the invention comprises methods for producing a male sterile turfgrass plant, an herbicide resistant turfgrass plant, an insect resistant turfgrass plant, a disease resistant turfgrass plant, a water stress tolerant turfgrass plant, a heat stress tolerant turfgrass plant, and a turfgrass plant with improved shelf-life. Said methods comprise transforming a turfgrass variety of the present invention, such as '03-0582', '03-0441', or '99-2495' plant with a nucleic acid molecule that confers male sterility, herbicide resistance, insect resistance, disease resistance, water stress tolerance, heat stress tolerance, or improved shelf life, respectively. The transformed turfgrass plants, or part(s) thereof, obtained from the provided methods, including a male sterile turfgrass plant, an herbicide resistant turfgrass plant, an insect resistant turfgrass plant, a disease resistant turfgrass plant, a turfgrass plant tolerant to water stress, a turfgrass plant tolerant to heat stress or a turfgrass plant with improved shelf-life are included in the present invention. For the present invention and the skilled artisan, disease is understood to be fungal diseases, viral diseases, bacterial diseases or other plant pathogenic diseases and a disease resistant plant will encompass a plant resistant to fungal, viral, bacterial and other plant pathogens.

In another aspect, the present invention provides for methods of introducing one or more desired trait(s) into turfgrass varieties having desirable looking turf when mowed infrequently, such as bluegrass varieties '03-0582', '03-0441', or '99-2495' and plants obtained from such methods. The desired trait(s) may be, but not exclusively, a single gene, preferably a dominant but also a recessive allele. Preferably, the transferred gene or genes will confer such traits as male sterility, herbicide resistance, insect resistance, resistance to bacterial, fungal, or viral disease, increased leaf number, improved shelf-life, and tolerance to water stress or heat stress. The gene or genes may be naturally occurring gene(s) or transgene(s) introduced through genetic engineering techniques. The method for introducing the desired trait(s) is preferably a backcrossing process making use of a series of backcrosses to turfgrass plants having desirable looking turf when mowed infrequently, such as bluegrass variety '03-0582', '03-0441', or '99-2495' during which the desired trait(s) is maintained by selection.

In a preferred embodiment, the present invention provides methods for increasing and producing turfgrass varieties having desirable looking turf when mowed infrequently, such as bluegrass varieties '03-0582', '03-0441', or '99-2495' seed, whether by crossing a first parent bluegrass variety plant with a second parent bluegrass variety plant and harvesting the resultant bluegrass seed, wherein both said first and second parent bluegrass variety plant are the bluegrass variety '03-0582', '03-0441', or '99-2495' or by planting a bluegrass seed of the bluegrass variety '03-0582', '03-0441', or '99-2495', growing a bluegrass variety '03-0582', '03-0441', or '99-2495' plant from said seed, controlling a self pollination of the plant where the pollen produced by a grown bluegrass variety '03-0582', '03-0441', or '99-2495' plant pollinates the ovules produced by the very same bluegrass variety '03-0582', '03-0441', or '99-2495' grown plant, and harvesting the resultant seed.

The invention further provides methods for developing turfgrass and Kentucky bluegrass cultivars having desirable looking turf when mowed infrequently in a turfgrass breeding program using plant breeding techniques including recurrent selection, backcrossing, pedigree breeding, molecular markers (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection, and transformation. Seeds, turfgrass plants, and part(s) thereof produced by such breeding methods are also part of the invention.

In addition to the exemplary aspects and embodiments described above, further aspects and embodiments will become apparent by study of the following descriptions.

BRIEF DESCRIPTION OF THE DRAWINGS

FIG. 1 shows the results of regression analysis that was performed to correlate visual turfgrass quality ratings with Field Scout CM 1000™ scan results for test plots mowed three times per year in Idaho. Regression analysis indicated that a visual quality estimate of 5 corresponds to a CM 1000™ meter reading of 341.7, with an unexpectedly high correlation co-efficient of 0.86, and an $R^2$ value of 0.73, which was significant at the 0.0001 level. In FIG. 1, circles represent individual observations, a solid line indicates regression fit to the data, and dashed lines indicate 95% confidence intervals.

DETAILED DESCRIPTION OF THE INVENTION

In the description and examples that follow, a number of terms are used. In order to provide a clear and consistent understanding of the specification and claims, including the scope to be given such terms, the following definitions are provided. If no definition is provided, all other technical and scientific terms used herein have the same meaning as is commonly understood by one of skill in the art to which the invention belongs.

Acceptable level of apomixes. Refers to 80% or higher level of apomixes.

Adequate production of seed heads. Refers to 15 grams or more of clean seed recovered from one individual spaced plant.

Allele. An allele is any of one or more alternative forms of a gene which relate to one trait or characteristic. In a diploid cell or organism, the two alleles of a given gene occupy corresponding loci on a pair of homologous chromosomes.

Alter. Alter refers to the utilization of up-regulation, down-regulation, or gene silencing.

Apomictic. As used herein, "apomictic" describes a plant that reproduces using apomixis Apomixis. Asexual reproduction in organisms that are also able to reproduce sexually, in which embryos are formed without fertilization or the creation of specialized reproductive cells.

Backcrossing. Backcrossing is a process in which a breeder repeatedly crosses hybrid progeny back to one of the parents, for example, a first generation hybrid $F_1$ with one of the parental genotypes of the $F_1$ hybrid.

Cell. Cell as used herein includes a plant cell, whether isolated, in tissue culture or incorporated in a plant or plant part.

Characteristics different from the maternal parental line. As used herein, refers to characteristics that are different from the maternal parental line, including but not limited to color and width of the leaves prior to seedhead expression and a different date when the seedhead emerges from the sheath of the turfgrass.

Chlorophyll concentration. The milligrams per gram of chlorophyll contained in plant tissue weight. Also referred to as "chlorophyll content".

Chlorophyll meter reading. The digital readout of the CM 1000™ chlorophyll field scanner.

Cisgenesis. The genetic modification of a recipient plant with a natural gene from a sexually compatible plant. Such a gene includes its introns and is flanked by it native promoter and terminator in the normal sense orientation. Cisgenic plants can harbor one or more cisgenes, but they do not contain any trangenes.

Cisgenic plant. A plant that contains no foreign genes.

Commercial perennial bluegrass. A commercial perennial bluegrass is one which has been sold commercially.

Cotyledon. A cotyledon is a seed leaf.

Crossbreeding. As used herein, "crossbreeding" refers to the act of mating (crossing) individuals of different species or varieties of plants to produce hybrids.

Crown. The crown in grass is the area at which top growth and root growth originate.

Culm. The culm is the main aerial shoot to which leaves and inflorescences are attached. The culm is a rounded or slightly flattened stem with one or more solid joints known as nodes. The leaves are attached at the nodes and if the stem is not simple but branched, branches arise only at nodes. Roots may also develop from a node where the node comes into contact with the ground (as in decumbent and prostrate stems).

Desirable looking turf. As used herein, "desirable looking turf" is quantified by an increased chlorophyll concentration of greater than 1.8 mg/g indicating the turf retention of green color even when scalped back (severely defoliated) by infrequent mowing. The chlorophyll concentration is additionally quantified by a CM-1000™ field chlorophyll reading of 341.7 or higher. "Turf" refers to any type of turfgrass, including bluegrass.

Embryo. The embryo is the small plant contained within a mature seed.

Endophyte. The term endophyte is applied to fungi which live within plant tissues for all or part of their lifecycle and cause no apparent infections.

Famigenic plant. A transformed plant developed by transferring at least some DNA from one plant to a sexually incompatible plant that belongs to the same family.

Field hybridization nursery. A spaced plant field breeding nursery having access to plants that grew from one seed, wherein a mother plant is surrounded by clones of itself (selfing) or a mother plant is surrounded by clones that are different than the mother plant (intraspecific hybridization).

Field Scout CM 1000™ chlorophyll meter. A "point-and-shoot" device to instantly measure relative chlorophyll content. The CM 1000™ senses light at wavelengths of 700 nm and 840 nm to estimate the quantity of chlorophyll in leaves. The ambient and reflected light at each wavelength is measured. Made by Spectrum Technologies, Inc., Plainfield, Ill.

Gene. As used herein, "gene" refers to a DNA segment that contributes to phenotype/function, including associated regulatory elements such as promoters. A gene can be introduced into a genome of a species, whether from a different species or from the same species, using transformation or various breeding methods.

Gene silencing. The interruption or suppression of the expression of a gene at the level of transcription or translation.

Genotype. Refers to the genetic constitution of a cell or organism.

Grass flower or inflorescence. Flowers of grasses are borne in an inflorescence or flower head which terminates the culm and other branches of the stem. Smaller units of the inflorescence are called spikelets and these are arranged on one or more branches in a wide variety of different ways to which the standard terminology for inflorescences can be applied, but using the spikelet instead of the individual flower.

Growing season. As used herein, "growing season" refers to the time of year during which turfgrass is actively growing, which is typically spring through fall in the U.S. and Europe.

Hybrid. Heterozygous offspring of two parents that differ in one or more inheritable characteristics.

Hypocotyl. A hypocotyl is the portion of an embryo or seedling between the cotyledons and the root. Therefore, it can be considered a transition zone between shoot and root.

Intragenic plant. A transformed plant that only contains genetic elements derived from within the sexual compatibility group.

Intergenic DNA. Any of the DNA in between gene-coding DNA, including untranslated regions, 5' and 3' flanking regions, introns, non-functional pseudogenes, and non-functional repetitive sequences. This DNA may or may not encode regulatory functions.

Internode. The internodes act as spacers that distance one node from another.

Intercalary meristem. Intercalary meristem is a meristem at the base of the internode in monocot stems (particularly grass stems).

Lawn. A plot of grass, usually tended or mowed, such as one near a house, on an estate, in a yard, garden or park, or a golf course, or any other such area covered with grass.

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Mature sod. Means sod that is 8 to 14 months old after seeding, wherein sod is mature at 8 to 11 months old after a fall seeding and sod is mature at 12 to 14 months old after a spring seeding.

Mowed infrequently. As used herein, "mowed infrequently" or "infrequently mowed" refers to grass that has been subjected to mowing with a conventional lawnmower once every four weeks or longer, such as once every 30, 32, 34, 36, 38, 39, 40 or more days, or any integer or fraction thereof.

Node. A node in a grass stem is a solid point at which the intercalary meristem is located. The node also contains the bud that is capable of producing a new shoot. The terminal node contains the bud that produces the inflorescence.

Pedigree distance. Pedigree distance refers to the relationship among generations based on their ancestral links as evidenced in pedigrees. Pedigree distance may be measured by the distance of the pedigree from a given starting point in the ancestry.

Percent identity. Percent identity as used herein refers to the comparison of the homozygous alleles of two perennial bluegrass varieties. Percent identity is determined by comparing a statistically significant number of the homozygous alleles of two developed varieties. For example, a percent identity of 90% between perennial bluegrass variety 1 and perennial bluegrass variety 2 means that the two varieties have the same allele at 90% of their loci.

Percent similarity. Percent similarity as used herein refers to the comparison of the homozygous alleles of one perennial bluegrass variety with another bluegrass plant, and if the homozygous allele of the first bluegrass matches at least one of the alleles from the other plant then they are scored as similar. Percent similarity is determined by comparing a statistically significant number of loci and recording the number of loci with similar alleles as a percentage. A percent similarity of 90% between the first bluegrass and another plant means that the first bluegrass matches at least one of the alleles of the other plant at 90% of the loci.

Plant. As used herein, the term "plant" includes reference to an immature or mature whole plant, including a plant from which seed, roots or leaves have been removed. Seed or embryo that will produce the plant is also considered to be the plant.

Plant height. The length of the grass leaf blade measured from the rhizome to the tip of the blade.

Plant parts. As used herein, the term "plant parts" (or a perennial bluegrass plant, or a part thereof) includes protoplasts, leaves, stems, roots, root tips, anthers, pistils, seed, embryo, pollen, ovules, cotyledon, hypocotyl, flower, shoot, tissue, petiole, cells, meristematic cells and the like.

Polynucleotide. A polymeric compound, usually DNA or RNA, consisting of a number of nucleotides.

Primary tillers. Primary tillers are shoots arising at the crown.

Progeny. As used herein, includes an $F_1$ turfgrass plant produced from the cross of two turfgrass plants where at least one plant includes a turfgrass plant of the present invention and progeny further includes, but is not limited to, subsequent $F_2, F_3, F_4, F_5, F_6, F_7, F_8, F_9$, and $F_{10}$ generational crosses with the recurrent parental line. As used herein, progeny also refers to plants produced by selfing a turfgrass plant produced by the present invention.

Promoter. A segment of DNA usually occurring upstream from a gene coding region and acting as a controlling element in the expression of that gene.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Rhizome. A rhizome is a modified stem that grows underground. Rhizomes are jointed (thus distinguishable from roots) with bladeless leaves (scales) arising from the joints Rhizomes enable a grass plant to spread horizontally as new culms develop vertically from the joints. Thus, grasses with extensive rhizome development will form a turf rather than distinct tufts or bunches.

Scalped back (severely defoliated). Refers to mowing of turfgrass wherein greater than one third of the leaf area is removed.

Secondary tillers. Secondary tillers are tillers arising as branches of the primary tillers.

Seedhead. The flowering (reproductive) part of the grass plant.

Seedhead expression. Refers to the emergence, full expression and maturation of the seedhead.

Selfing. Pollinating a plant and hybridizing it with its own pollen or pollen from a clone of that plant.

Short, basal growth of leaves. Refers to a preponderance of green leaf material in the 0 to 4 inch zone above the soil surface.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Sod. A section of grass-covered surface soil held together by matted roots; turf.

Stolon. A stolon is a stem that creeps across the surface of the ground, and is really a basal branch of the culm that will develop roots and shoots from some or all of its nodes. Like a rhizome, a stolon results in a spreading or turf forming grass plant.

Tensile strength. Means the amount of force in pounds required to tear a piece of sod in two. Tensile strength is determined with a mechanical sod stretcher coupled to a device to measure force in pounds. Tensile strength, tear point and sod strength are used interchangeably.

Tiller. A tiller is another name for a grass stem.

Tiller length. Tiller length is measured in centimeters from the lowest node to the last node subtending the green foliage.

Transgene. A gene that is transferred from an organism of one species to an organism of another species by genetic engineering.

Variant. As used herein, refers to offspring that occur in a naturally apomictic species by means of hybridization of pollen and ovule, resulting in offspring with some but not all characteristics of the maternal parent plant.

Variety. A taxonomic subdivision of a species consisting of naturally occurring or selectively bred populations or individuals that differ from the remainder of the species in certain minor characteristics.

Vernalization. Vernalization induces plants to begin the reproductive cycle after exposure to cold temperatures and short day length. The amount of cold exposure and short day lengths required varies with the species.

Xenogenic modification. Introduction of powerful new traits that might outperform native traits by transforming plants with synthetic genes.

The following detailed description is of the currently contemplated modes of carrying out the invention. The description is not to be taken in a limiting sense, but is made merely for the purpose of illustrating the general principles of the invention, since the scope of the invention is best defined by the appended claims.

Broadly, the present invention is directed toward turfgrass varieties, including both plants and seeds, having desirable looking turf when mowed infrequently. The turfgrass varieties of the present invention were developed to retain a dark green color even when scalped back by infrequent mowing. Part of this tolerance traces to the method of breeding, which stresses low growing plants, with foliage tight to the ground. However, there are also other traits that are less quantitative that convey infrequent mowing tolerance, such as the physiological ability to withstand defoliation and recover without discoloration or objectionable stunting. In essence, these plants do not just grow vertically slower than other varieties, they also possess growth characteristics that allow them to endure on a infrequently mowed lawn while maintaining a desirable looking turf.

In the field hybridization nursery, individual spaced plants are identified with promising characteristics such as the short growth of leaves (defined as a preponderance of green leaf material in the 0 to 4 inch zone above the soil surface), adequate seed heads (defined as 15 g or more of clean seed recovered from one individual spaced plant), and acceptable apomixes (defined as 80% or higher). These promising plants are individually hand harvested and cleaned of chaff and seed are planted in replicated turf trials, subject to mowing once every 4 weeks or longer. Each plot in the experiment is evaluated monthly during the growing season, using a visual rating scale of 1 to 9, where 9 is highly desirable turf and 5 is minimal acceptable quality, and 1 is totally brown or dead. During one or more evaluation dates, the chlorophyll meter is used to evaluate plots to impartially differentiate green tissue from lifeless brown tissue created from the scalping process.

Most turfgrass managers practice the "one third rule" for clipping lawns and golf courses. The "one third rule" states that a maximum of one third of the leaf area should be removed during any one mowing. Deviating from this "one third rule" could lead to an unacceptable quantity of the plant's photosynthetic surface being removed. As a result, the plant goes into a shock mode and sacrifices leaves in exchange for survival. Plant varieties that grow vertically very tall or extremely fast are more subject to damage from defoliation. The visual result is that the plant rapidly turns brown within 24 hours and may take days or weeks to recover. An additional result of this shock is the loss of shoot density of the plant, defined as the number of live vegetative shoots per square centimeter of ground surface. The present invention described herein deals with plants that do not exhibit this browning shock when they are subject to infrequent mowing.

The present invention provides a method of producing a turfgrass plant having desirable-looking turf when mowed infrequently, said method comprises selfing (pollinating a plant and hybridizing it with its own pollen) for one or more generations to create a plant with short growth of leaves (defined as a preponderance of green leaf material in the 0 to 4 inch zone above the soil surface), adequate seed heads (defined as 15 g or more of clean seed recovered from one individual spaced plant), and acceptable apomixes (defined as 80% or higher). The hybridization can take place in a confined greenhouse using pollen restricting bags, or take place in the field surrounded by clones of the same genotype, or any combination of these two methods. The progeny of said hybridizations are then field screened for approximately 15 months to identify plants with characteristics different than the maternal parent line; such differences are most commonly identified during the vegetative or pre-seedhead phase, but also may be identified during seedhead expression. The method of the present invention unexpectedly produced turfgrass plants having very basal growth habit, with leaves growing close to the ground rather than growing tall, which have desirable-looking turf when mowed infrequently.

It should be understood, of course, that the foregoing relates to exemplary embodiments of the invention and that modifications may be made without departing from the spirit and scope of the invention as set forth in the following claims.

Further Embodiments of the Invention

Choice of breeding or selection methods depends on the mode of plant reproduction, the heritability of the trait(s) being improved, and the type of cultivar used commercially (e.g., $F_1$ hybrid cultivar, pureline cultivar, etc.). Popular selection methods commonly include population formation by hybridization, genomic selection, marker assisted selection, recurrent selection, mutation breeding, single-seed descent, bulk selection, pedigree selection, modified pedigree selection, and mass selection.

Breeding Methods

The following describes breeding methods that may be used with the turfgrass varieties of the present invention having desirable looking turf when mowed infrequently, such as bluegrass varieties '03-0582', '03-0441', or '99-2495' in the development of further bluegrass plants. One such embodiment is a method for developing a cultivar '03-0582', '03-0441', or '99-2495' progeny bluegrass plant in a bluegrass plant breeding program comprising: obtaining the bluegrass plant, or a part thereof, of cultivar '03-0582', '03-0441', or '99-2495' utilizing said plant or plant part as a source of breeding material and selecting a bluegrass cultivar '03-0582', '03-0441', or '99-2495' progeny plant with molecular markers in common with variety '03-0582', '03-0441', or '99-2495' and/or with morphological and/or physiological characteristics described herein.

Another method involves producing a population of turfgrass varieties of the present invention having desirable looking turf when mowed infrequently, such as bluegrass varieties '03-0582', '03-0441', or '99-2495' progeny bluegrass plants, comprising crossing cultivar '03-0582', '03-0441', or '99-2495' with another bluegrass plant, thereby producing a population of bluegrass plants, which, on average, derive 50% of their alleles from bluegrass variety '03-0582', '03-0441', or '99-2495'. A plant of this population may be selected and repeatedly selfed or sibbed with a bluegrass cultivar resulting from these successive filial generations. In some embodiments, the bluegrass cultivar produced by this method and that has obtained at least 50% of its alleles from bluegrass variety '03-0582', '03-0441', or '99-2495'.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the methods and variety described herein includes turfgrass plants having desirable looking turf when mowed infrequently, such as bluegrass cultivar '03-0582', '03-0441', or '99-2495' progeny bluegrass plants comprising a combination of at least two cultivar '03-0582', '03-0441', or '99-2495' traits or the cultivar '03-0582', '03-0441', or '99-2495' combination of traits listed in the Examples, so that said progeny bluegrass plant is not significantly different for said traits than bluegrass variety '03-0582', '03-0441', or '99-2495' as determined at the 5% significance level when grown in the same environmental conditions. Using techniques described herein, molecular markers may be used to identify said progeny plant as a bluegrass variety '03-0582', '03-0441', or '99-2495' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of turfgrass plants of the present invention having desirable looking turf when mowed infrequently, such as bluegrass variety '03-0582', '03-0441', or '99-2495' may also be characterized through their filial relationship with bluegrass variety '03-0582', '03-0441', or '99-2495', as for example, being within a certain number of breeding crosses of bluegrass variety '03-0582', '03-0441', or '99-2495'. A breeding cross is a cross made to introduce new genetics into the progeny, and is distinguished from a cross, such as a self or a sib cross, made to select among existing genetic alleles. The lower the number of breeding crosses in the pedigree, the closer the relationship between bluegrass variety '03-0582', '03-0441', or '99-2495' and its progeny. For example, progeny produced by the methods described herein may be within 1, 2, 3, 4 or 5 breeding crosses of bluegrass variety '03-0582', '03-0441', or '99-2495'.

Recurrent selection is a method used in a plant breeding program to improve a population of plants. Turfgrass having desirable looking turf when mowed infrequently, such as '03-0582', '03-0441', or '99-2495' is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties. The number of parental plant varieties, populations, wild accessions, ecotypes, etc., that are used to generate a synthetic can vary from as little as 10 to as much as 500. Typically, about 100 to 300 varieties, populations, etc., are used a parents for the synthetic variety. Seed from the parental seed production plot of a synthetic variety can be sold to the farmer. Alternatively, seed from the parental seed production plot can subsequently undergo one or two generations of multiplication, depending on the amount of seed produced in the parental plot and the demand for seed.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation breeding is another method of introducing new traits into turfgrass plants having desirable looking turf when mowed infrequently, such as bluegrass variety '03-0582', '03-0441', or '99-2495'. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (such as from 2500 to 2900 nm), or chemical mutagens (such as base analogues (5-bromouracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, 1993. Principles of Cultivar Development, Macmillan Publishing Company. In addition, mutations created in other bluegrass plants may be used to produce a backcross conversion of bluegrass variety '03-0582', '03-0441', or '99-2495' that comprises such mutation.

Breeding with Molecular Markers

Molecular markers, which include markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing bluegrass variety '03-0582', '03-0441', or '99-2495'.

Isozyme Electrophoresis and RFLPs have been widely used to determine genetic composition. Shoemaker and Olsen, (O'Brien, S. J., (ed.) 1993. Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also, Shoemaker R. C. 1994. "RFLP Map of Soybean" p 299-309 In R. L. Phillips and I. K. Vasil (ed.) DNA-Based Markers in Plants. Kluwer Academic Press Dordrecht, the Netherlands. In switchgrass, Missaoui also described RFLP markers (Missaoui et al., 2006, "Molecular markers for the classification of switchgrass (*Panicum virgatum* L.) germplasm and to assess genetic diversity in three synthetic switchgrass populations" Genetic Resources and Crop Evolution 53:1291-1302).

SSR technology is currently the most efficient and practical marker technology; more marker loci can be routinely used and more alleles per marker locus can be found using SSRs in comparison to RFLPs. For example Diwan and Cregan, described a highly polymorphic microsatellite loci in soybean with as many as 26 alleles. (Diwan, N., and P. B. Cregan. 1997 "Automated sizing of fluorescent-labeled simple sequence repeat (SSR) markers to assay genetic variation in soybean". Theor. Appl. Genet. 95:220-225). Single Nucleotide Polymorphisms (SNPs) may also be used to identify the unique genetic composition of '03-0582', '03-0441', or '99-2495' and progeny varieties retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Gene Conversions

When the term "turfgrass plant" or "bluegrass plant" is used in the context of the methods and varieties described herein, this also includes any gene conversions of that variety. The term gene converted plant as used herein refers to those turfgrass plants which are developed by a plant breeding technique called backcrossing wherein essentially all of the desired morphological and physiological characteristics of a variety are recovered in addition to the one or more genes transferred into the variety via the backcrossing technique. Backcrossing methods can be used with the methods and variety described herein to improve or introduce one or more characteristics into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental turfgrass plant that contributes the gene(s) for the desired characteristic is termed the nonrecurrent or donor parent. This terminology refers to the fact that the nonrecurrent parent is used one time in the backcross protocol and therefore does not recur. The parental turfgrass plant to which the gene or genes from the nonrecurrent parent are transferred is known as the recurrent parent as it is used for several rounds in the backcrossing protocol (Poehlman & Sleper, 1994; Fehr, Principles of Cultivar Development pp. 261-286 (1987)). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a turfgrass plant is obtained wherein essentially all of the desired morphological and physiological characteristics of the recurrent parent are recovered in the converted plant, in addition to the transferred gene(s) from the nonrecurrent parent.

The selection of a suitable recurrent parent is an important step for a successful backcrossing procedure. The goal of a backcross protocol is to alter or substitute one or more traits or characteristics in the original variety. To accomplish this, one or more genes of the recurrent variety is/are modified or substituted with the desired gene(s) from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic(s) or trait(s) being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic(s) has been successfully transferred.

Many traits have been identified that are not regularly selected for in the development of a new variety but that can be improved by backcrossing techniques. Traits may or may not be transgenic; examples of these traits include but are not limited to, male sterility, herbicide resistance, resistance for bacterial, fungal, or viral disease, insect resistance, male fertility, enhanced nutritional quality, modified oil content, industrial usage, yield stability and yield enhancement. These genes are generally inherited through the nucleus. Several of these traits are described in U.S. Pat. Nos. 5,959,185; 5,973,234 and 5,977,445; the disclosures of which are specifically hereby incorporated by reference for this purpose.

Introduction of a New Trait or Locus into Turfgrass Plants Having Desirable Looking Turf when Mowed Infrequently, Such as '03-0582', '03-0441', or '99-2495'

Turfgrass plants of the present invention having desirable looking turf when mowed infrequently, such as variety '03-0582', '03-0441', or '99-2495' represent a new base genetic variety into which a new locus or trait may be introgressed. Direct transformation and backcrossing represent two important methods that can be used to accomplish such an introgression. The term backcross conversion and locus conversion are used interchangeably to designate the product of a backcrossing program.

Backcross Conversions of Turfgrass Plants Having Desirable Looking Turf when Mowed Infrequently, Such as '03-0582', '03-0441', or '99-2495'

A backcross conversion of turfgrass plants of the present invention having desirable looking turf when mowed infrequently, such as '03-0582', '03-0441', or '99-2495' occurs when DNA sequences are introduced through backcrossing (Poehlman, Breeding Field Crops, p. 204 (1987), with '03-0582', '03-0441', or '99-2495' utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., "Marker-assisted Selection in Backcross Breeding" In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes vs unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in Corn and Corn Improvement, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, altered carbohydrate profile, modified oil production, industrial enhancements, disease resistance (bacterial, fungal or viral), insect resistance and herbicide resistance. In addition, an introgression site itself, such as an FRT site, Lox site or other site-specific integration site, may be inserted by backcrossing and utilized for direct insertion of one or more genes of interest into a specific plant variety. In some embodiments, the number of loci that may be backcrossed into '03-0582', '03-0441', or '99-2495' is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of a site-specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, Breeding Field Crops, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

One process for adding or modifying a trait or locus in turfgrass plants of the present invention having desirable looking turf when mowed infrequently, such as bluegrass variety '03-0582', '03-0441', or '99-2495' comprises crossing '03-0582', '03-0441', or '99-2495' plants grown from '03-0582', '03-0441', or '99-2495' seed with plants of another bluegrass variety that comprise the desired trait or locus, selecting $F_1$ progeny plants that comprise the desired trait or locus to produce selected $F_1$ progeny plants, crossing the selected progeny plants with the '03-0582', '03-0441', or '99-2495' plants to produce backcross progeny plants, selecting for backcross progeny plants that have the desired trait or locus and the morphological characteristics of bluegrass variety '03-0582', '03-0441', or '99-2495' to produce selected backcross progeny plants; and backcrossing to '03-0582', '03-0441', or '99-2495' three or more times in succession to produce selected fourth or higher backcross progeny plants that comprise said trait or locus. The modified '03-0582', '03-0441', or '99-2495' may be further characterized as having the physiological and morphological characteristics of bluegrass variety '03-0582', '03-0441', or '99-2495' and/or may be characterized by percent similarity or identity to '03-0582', '03-0441', or '99-2495' as determined by SSR markers. The above method may be utilized with fewer backcrosses in appropriate situations, such as when the donor parent is highly related or markers are used in the selection step. Desired traits that may be used include those nucleic acids known in the art, some of which are mentioned herein, that will affect traits through nucleic acid expression or inhibition. Desired loci include the introgression of FRT, Lox and other sites for site specific integration, which may also affect a desired trait if a functional nucleic acid is inserted at the integration site.

Pedigree Breeding

Pedigree breeding starts with the crossing of two genotypes, such as turfgrass plants of the present invention having desirable looking turf when mowed infrequently, such as '03-0582', '03-0441', or '99-2495' and another bluegrass variety having one or more desirable characteristics that is lacking or which complements '03-0582', '03-0441', or '99-2495'. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. In some embodiments, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a turfgrass variety may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the non-recurrent parent. This approach leverages the value and strengths of the recurrent parent for use in new turfgrass varieties.

Therefore, an embodiment is a method of making a backcross conversion of turfgrass plants of the present invention having desirable looking turf when mowed infrequently, such as bluegrass variety '03-0582', '03-0441', or '99-2495', comprising the steps of crossing a plant of bluegrass variety '03-0582', '03-0441', or '99-2495' with a donor plant comprising a desired trait, selecting an $F_1$ progeny plant comprising the desired trait, and backcrossing the selected $F_1$ progeny plant to a plant of bluegrass variety '03-0582', '03-0441', or '99-2495'. This method may further comprise the step of obtaining a molecular marker profile of bluegrass variety '03-0582', '03-0441', or '99-2495' and using the molecular marker profile to select for a progeny plant with the desired trait and the molecular marker profile of '03-0582', '03-0441', or '99-2495'. In one embodiment the desired trait is a mutant gene or transgene present in the donor parent.

In addition, the above process and other similar processes described herein may be used to produce first generation progeny bluegrass seed by adding a step at the end of the process that comprises crossing turfgrass plants of the present invention having desirable looking turf when mowed infrequently, such as '03-0582', '03-0441', or '99-2495' with the introgressed trait or locus with a different bluegrass plant and harvesting the resultant first generation progeny bluegrass seed.

Transgenic Turfgrass

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation are referred to herein collectively as "transgenes". In some embodiments of the invention, transgenic variants of the turfgrass varieties of the present invention may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed turfgrass varieties of the present invention.

Genetic engineering of the plants of the present invention includes various methods for crop improvement, including transgenic modification, xenogenic modification, intragenic modification, famigenic modification and cisgenic modification.

One embodiment of the invention is a process for producing turfgrass varieties further comprising a desired trait, said process comprising transforming a turfgrass plant with a transgene that confers a desired trait. Another embodiment is the product produced by this process. In one embodiment the desired trait may be one or more of herbicide resistance, insect resistance, disease resistance or modified fatty acid or carbohydrate metabolism. In one embodiment the desired trait may be increased or modified oil content. The specific gene may be any known in the art or listed herein, including: a polynucleotide conferring resistance to imidazolinone, sulfonylurea, glyphosate, glufosinate, triazine, benzonitrile, cyclohexanedione, phenoxy proprionic acid and L-phosphinothricin; a polynucleotide encoding a *Bacillus thuringiensis* polypeptide, or a polynucleotide conferring resistance to one or more nematodes, *Phytophthora* root rot, or other fungi, or one or more viruses.

Numerous methods for plant transformation have been developed, including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

A genetic trait which has been engineered into the genome of a particular turfgrass plant may then be moved into the genome of another turfgrass variety using traditional breeding techniques that are well known in the plant breeding arts. For example, a backcrossing approach is commonly used to move a transgene from a transformed bluegrass variety into an already developed bluegrass variety, and the resulting backcross conversion plant would then comprise the transgene(s).

Various genetic elements can be introduced into the plant genome using transformation. These elements include, but are not limited to genes, coding sequences, inducible, constitutive, and tissue specific promoters, enhancing sequences, and signal and targeting sequences. For example, see the traits, genes and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed turfgrass plants using transformation methods as described below to incorporate transgenes into the genetic material of the turfgrass plant(s).

With transgenic plants according to the methods and variety described herein, a foreign or endogenous protein or oil can be produced in commercial quantities. Thus, techniques for the selection and propagation of transformed plants, which are well understood in the art, yield a plurality of transgenic plants which are harvested in a conventional manner, and a foreign or endogenous protein or oil then can be extracted from a tissue of interest or from total biomass. Protein extraction from plant biomass can be accomplished by known methods which are discussed, for example, by Heney and Orr, *Anal. Biochem.* 114:92-6 (1981).

According to a one embodiment, the transgenic plant provided for commercial production of foreign or endogenous protein or oil is a turfgrass plant. In another embodiment, the biomass of interest is leaves, stems, or other plant parts. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant.

Expression Vectors for Turfgrass Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., Proc. Natl. Acad. Sci. USA, 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986)). Other selectable marker genes confer resistance to herbicides such as glyphosate, glufosinate or bromoxynil (Comai et al., Nature 317:741-744 (1985), Gordon-Kamm et al., Plant Cell 2:603-618 (1990) and Stalker et al., Science 242:419-423 (1988)).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., Somatic Cell Mol. Genet. 13:67 (1987), Shah et al., Science 233:478 (1986), Charest et al., Plant Cell Rep. 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include $\beta$-glucuronidase (GUS), $\beta$-galactosidase, luciferase and chloramphenicol acetyltransferase (Jefferson, R. A., Plant Mol. Biol. Rep. 5:387 (1987), Teeri et al., EMBO J. 8:343 (1989), Koncz et al., Proc. Natl. Acad. Sci. USA 84:131 (1987), DeBlock et al., EMBO J. 3:1681 (1984)).

In vivo methods for visualizing GUS activity that do not require destruction of plant tissue are available (Molecular Probes publication 2908, IMAGENE GREEN, p. 1-4 (1993) and Naleway et al., J. Cell Biol. 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., Science 263: 802 (1994)). GFP and mutants of GFP may be used as screenable markers.

Expression Vectors for Turfgrass Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner. Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996). Examples of various regulatory regions are described in more detail in U.S. Patent Application Ser. Nos. US20080072340, US20080044898, US20070277269, US20070226830, US20070136839, US 20070124834, and US 20060107346. It will be appreciated that a regulatory region may meet criteria for one classification based on its activity in one plant species, and yet meet criteria for a different classification based on its activity in another plant species. Examples of regulatory regions include broadly expressing promoters, root promoters, maturing endosperm promoters, ovary tissue promoters, embryo sac/early endosperm promoters, embryo promoters, photosynthetic tissue promoters, vascular tissue promoters, inducible promoters, basal promoters, or other regulatory regions.

A. Inducible Promoters—An inducible promoter is operably linked to a gene for expression in turfgrass. Optionally, the inducible promoter is operably linked to a nucleotide sequence encoding a signal sequence which is operably linked to a gene for expression in perennial turfgrass. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., Proc. Natl. Acad. Sci. USA 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., Proc. Natl. Acad. Sci. USA 88:0421 (1991)).

B. Constitutive Promoters—A constitutive promoter is operably linked to a gene for expression in turfgrass or the constitutive promoter is operably linked to a nucleotide sequence encoding a signal sequence which is operably linked to a gene for expression in turfgrass.

Many different constitutive promoters can be utilized in the instant invention. Exemplary constitutive promoters include, but are not limited to, the promoters from plant viruses such as the 35S promoter from CaMV (Odell et al., Nature 313:810-812 (1985)) and the promoters from such genes as rice actin (McElroy et al., Plant Cell 2: 163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT application WO 96/30530.

C. Tissue-specific or Tissue-preferred Promoters—A tissue-specific promoter is operably linked to a gene for expression in turfgrass. Optionally, the tissue-specific promoter is operably linked to a nucleotide sequence encoding a signal sequence which is operably linked to a gene for expression in turfgrass. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., Science 23:476-482 (1983) and Sengupta-Gopalan et al., Proc. Natl. Acad. Sci. USA 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

Transport of a protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., Plant Mol. Biol. 20:49 (1992); Knox, C., et al., Plant Mol. Biol. 9:3-17 (1987); Lerner et al., Plant Physiol. 91:124-129 (1989); Frontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

Wang et al. discuss "Large Scale Identification, Mapping and Genotyping of Single-Nucleotide Polymorphisms in the Human Genome", *Science,* 280:1077-1082, 1998, and similar capabilities are becoming available for the bluegrass genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of interest. Through the transformation of turfgrass the expression of genes can be altered to enhance disease resistance, insect resistance, herbicide resistance and other traits, such as oil content. DNA sequences native to turfgrass as well as non-native DNA sequences can be transformed into turfgrass and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) *PNAS USA* 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Likewise, by means of the present invention, additional genes of interest can be expressed in transformed plants. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al. *Cell* 78:1089 (1994) (*Arabidopsis* RSP2 gene for resistance to *Pseudomonas syringae*), McDowell & Woffenden, (2003) *Trends Biotechnol.* 21(4): 178-83 and Toyoda et al., (2002) *Transgenic Res.* 11 (6):567-82.

B. A gene conferring resistance to a pest, such as a nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*); Chattopadhyay et al. (2004) *Critical Reviews in Microbiology* 30 (1): 33-54 2004; Zjawiony (2004) *J Nat Prod* 67 (2): 300-310; Carlini & Grossi-de-Sa (2002) *Toxicon,* 40 (11): 1515-1539; Ussuf et al. (2001) *Curr Sci.* 80 (7): 847-853; and Vasconcelos & Oliveira (2004)

Toxicon 44 (4): 385-403. See also U.S. Pat. No. 5,266,317 to Tomalski et al., which discloses genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene, U.S. Pat. Nos. 7,145,060, 7,087,810 and 6,563,020.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO 95/16776 and U.S. Pat. No. 5,580,852, which disclose peptide derivatives of tachyplesin which inhibit fungal plant pathogens, and PCT application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes et al., Plant Sci 89:43 (1993), of heterologous expression of a cecropin-β lytic peptide analog to render transgenic tobacco plants resistant to Pseudomonas solanacearum.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., Current Biology, 5(2) (1995); Pieterse & Van Loon (2004) Curr. Opin. Plant Bio. 7(4):456-64 and Somssich (2003) Cell 113(7):815-6.

U. Antifungal genes. See Cornelissen and Melchers, Plant Physiol., 101:709-712 (1993); Parijs et al., Planta 183:258-264 (1991) and Bushnell et al., Can. J. of Plant Path. 20(2): 137-149 (1998). Also see U.S. Pat. No. 6,875,907.

V. Detoxification genes, such as for fumonisin, beauvericin, moniliformin and zearalenone and their structurally related derivatives. For example, see U.S. Pat. No. 5,792,931.

W. Cystatin and cysteine proteinase inhibitors. See U.S. Pat. No. 7,205,453.

X. Defensin genes. See WO 03/000863 and U.S. Pat. No. 6,911,577.

Y. Genes that confer resistance to Phytophthora root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., Phytophthora Root Rot Resistance Gene Mapping in Soybean, Plant Genome IV Conference, San Diego, Calif. (1995).

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvylshikimate-3-phosphate synthase (EPSPS) and aroA genes, respectively) and other phosphono compounds such as glufosinate (phosphinothricin acetyl transferase (PAT) and Streptomyces hygroscopicus PAT bar genes), and pyridinoxy or phenoxy proprionic acids and cyclohexanediones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and U.S. Pat. No. 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. No. 10/427,692. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., *Theon. Appl. Genet.* 83:435 (1992).

C. An herbicide that inhibits photosynthesis, such as a triazine (psbA and gs+ genes) and a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

5. Genes that Create a Site for Site Specific DNA Integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of *E. coli* (Enomoto et al., 1983), and the R/RS system of the pSR1 plasmid (Araki et al., 1992).

6. Genes that Affect Abiotic Stress Resistance.

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. No. 10/817,483 and U.S. Pat. No. 6,992,237 where cytokinin expression is modified resulting in plants with increased stress tolerance, such as drought tolerance, and/or increased yield. Also see WO 02/02776, WO 2003/052063, JP2002281975, U.S. Pat. No. 6,084,153, WO 01/64898, U.S. Pat. Nos. 6,177,275 and 6,107,547 (enhancement of nitrogen utilization and altered nitrogen responsiveness). For ethylene alteration, see US 20040128719, US 20030166197 and WO 2000/32761. For plant transcription factors or transcriptional regulators of abiotic stress, see e.g. US 20040098764 or US 20040078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29123, U.S. Pat. No. 6,794,560, U.S. Pat. No. 6,307,126 (GAI), WO 99/09174 (D8 and Rht), and WO 2004/076638 and WO 2004/031349 (transcription factors).

Methods for Turfgrass Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994)).

Following transformation of bluegrass target tissues, expression of the above-described selectable marker genes allows for preferential selection of transformed cells, tissues and/or plants, using regeneration and selection methods well known in the art.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" *Crop Science* 39:1464-1490 (1999), and Berry et al., Assessing Probability of Ancestry Using Simple Sequence Repeat Profiles: Applications to Maize Inbred Lines and Soybean Varieties" *Genetics* 165:331-342 (2003).

Particular markers used for these purposes are not limited to any particular set of markers, but are envisioned to include any type of marker and marker profile which provides a means of distinguishing varieties.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Tissue Culture

Further reproduction of the turfgrass varieties of the present invention can occur by tissue culture and regeneration. Tissue culture of various tissues of turfgrass and regeneration of plants therefrom is well known and widely published. For example, reference may be had to Bradley, D. E. et al. 2001. Effects of cultivar, explant treatment, and medium supplements on callus induction and plantlet regeneration in perennial bluegrass. *Int. Turfgrass Soc. Res. J.* 9:152-156; Cao, M. X., et al. 2006. Transformation of recalcitrant turfgrass cultivars through improvement of tissue culture and selection regime. *Plant, Cell, Tissue Organ Culture.* 85:307-316; WenZhen, L. et al. Factors effecting on tissue culture of perennial ryegrass (*Lolium perenne* L.). *Forest Res.* 2004. 17:95-101 Thus, another aspect of this invention is to provide cells which upon growth and differentiation produce turfgrass plants having the physiological and morphological characteristics of the turfgrass plants of the present invention.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, culms, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

EXAMPLES

The following examples are provided to further illustrate the present invention and are not intended to limit the invention beyond the limitations set forth in the appended claims. The three cultivars listed below are the first in a series of new turfgrass varieties. The following descriptions characterize their breeding history, development, and the seed production characteristics of these cultivars.

Example 1

Method of Producing a Turfgrass Plant Having Desirable Looking Turf when Mowed Infrequently In the field hybridization nursery, individual spaced plants are identified with promising characteristics such as the short growth of leaves (defined as a preponderance of green leaf material in the 0 to 4 inch zone above the soil surface), adequate seed heads (defined as 15 g or more of clean seed recovered from one individual spaced plant), and acceptable apomixes (defined as 80% or higher). These promising plants are individually hand harvested and cleaned of chaff and seed are planted in replicated turf trials, subject to mowing once every 4 weeks or less frequent. Each plot in the experiment is evaluated monthly during the growing season, using a visual rating scale of 1 to 9, where 9 is highly desirable turf and 5 is minimal acceptable quality, and 1 is totally brown or dead. During one or more evaluation dates, the chlorophyll meter is used to evaluate plots to impartially differentiate green tissue from lifeless brown tissue created from the scalping process.

Most turfgrass managers practice the "one third rule" for clipping lawns and golf courses. The "one third rule" states that a maximum of one third of the leaf area should be removed during any one mowing. Deviating from this "one third rule" could lead to an unacceptable quantity of the plant's photosynthetic surface being removed. As a result, the plant goes into a shock mode and sacrifices leaves in exchange for survival. Plant varieties that grow vertically very tall or extremely fast are more subject to damage from defoliation. The visual result is that the plant rapidly turns brown within 24 hours and may take days or weeks to recover. An additional result of this shock is the loss of shoot density of the plant, defined as the number of live vegetative shoots per square centimeter of ground surface. The present invention described herein deals with plants that do not exhibit this browning shock when they are subject to infrequent mowing.

The present invention provides a method of producing a turfgrass plant having desirable-looking turf when mowed infrequently, said method comprises selfing (pollinating a plant and hybridizing it with its own pollen) for one or more generations to create a plant with short growth of leaves (defined as a preponderance of green leaf material in the 0 to 4 inch zone above the soil surface), adequate seed heads (defined as 15 g or more of clean seed recovered from one individual spaced plant), and acceptable apomixes (defined as 80% or higher). The hybridization can take place in a confined greenhouse using pollen restricting bags, or take place in the field surrounded by clones of the same genotype, or any combination of these two methods. The progeny of said hybridizations are then field screened for approximately 15 months to identify plants with characteristics different than the maternal parent line; such differences are most commonly identified during the vegetative or pre-seedhead phase, but also may be identified during seedhead expression, and include differences in color and width of the leaves prior to seedhead expression and a different date when the seedhead emerges from the sheath of said turfgrass genotype. The method of the present invention unexpectedly produced turfgrass plants having very basal growth habit, with leaves growing close to the ground rather than growing tall, which have desirable-looking turf when mowed infrequently.

Example 2

Development and Characteristics of Kentucky Bluegrass Plant '03-0582'

'03-0582' Kentucky bluegrass, also known by the designation 'J-0582', originated as a low-growing, apomictic, single-plant selection from the progeny of Jacklin Seed breeding line '98-2111'. Breeding line '98-2111' was self pollinated to produce '03-0582'. Breeding line '98-2111' originated as a selected low-growing progeny of breeding line '96-0305', first identified and harvested in the field in May 1996. Breeding line '96-0305' had a medium seed yield potential, 50% apomixis, medium-early reproductive maturity, and an average culm length of 45 cm. Based on the prior art, it was totally unexpected that a variety with low apomixes would give rise to a variety with acceptable or high levels of apomixes. Breeding line '96-0305' was a selection from the progeny of a hybrid cross between Absolute Kentucky bluegrass pollinated by BlueChip, created as a paired field cross.

Seed harvested from '03-0582' was used to establish infrequently mowed trials in Idaho in 2006, and in Maryland and Ohio in 2007. '03-0582' was selected for release based on its turf quality performance in all months of the year under twice yearly mowing, as well as its seed production characteristics in Washington State.

'03-0582' is an ideal plant form for infrequent mowing with low foliage and an unexpected proliferation of large dense seed heads on short strawed culms. At anthesis the stand and panicles have a yellowish green appearance with very little purplish coloration with the exception of the anthers. The panicles take on an almost whitish cast when seen from a distance; however, up close several of the florets and sometimes entire panicles have an appearance like they were dipped in diffuse purple dye. Spaced nursery plants are shaped like a cupcake with vertical, uniformly length straw and a proliferation of seed heads at the top. There is a difference in culm length by about 50% from the center to the perimeter of the plant. The foliage of the space plants is dark green in color and broad in width. Heading is considered medium in maturity however anthesis is occurring on the same day as with the later 5-Steps Above type varieties (e.g., NuGlade and Award).

Culms are smooth to the touch in both directions and medium green in color. Flag leaves are deep bluish green in color and relatively short. They are smooth to the touch in the upward direction and rough to the touch when felt in the direction toward the base. The flag leaf node junction is vertical with very little to no bend and little to no coloration difference from the culm itself. Panicles are small in size with a good number of florets that are medium to small in size. The panicles have numerous branches, more than some varieties and the branches are mostly oriented in the horizontal to downward direction with little to no waviness. The tips are mostly drooping, as are the second or third nodes from the tip; the rest are somewhat ascending. There is little to no influence of soil on seed head productivity except on the area of the field that received little to no water.

Progeny trials were conducted in spaced-plant nurseries, established June 2010, to determine the level of apomixis. A survey of 579 plants of '03-0582' showed that 4.2% of plants were variants in the vegetative (pre-flowering) stage, 1.7% were heading maturity variants, 0.3% were seedhead variants, 0% were variants appearing in the dry-down phase, and 2.5% were miniature plants. Many of the variants have shorter culms than the majority plant form with less purple panicle coloration. Variants may not be obvious in commercial seed production due to the masking effect of bulk populations. The spaced-plant apomixis rate of '03-0582' averages 91%, but it varies from year to year depending on growing conditions.

Variants in this variety appear primarily during the vegetative growth stage before heading. The majority of the variants have culm lengths equal to or shorter than the majority plant form and as such will be relatively inconspicuous in seed production. Soil variations make the variety appear non-uniform in places however this is an adjustment of the variety to soil and not a difference in genetics. Most of the variants have a similar vegetative form to the majority with the exception of more vertical or less vertical culm orientation. Approximately 2.5% of plants are miniature plants which will not be apparent in seed production.

'03-0582' Kentucky bluegrass is a stable and uniform variety. All seedlots evaluated have produced turf of comparable quality and acceptable uniformity. Aberrant progeny are rogued from Breeders, Foundation, and Registered fields to insure continued uniformity and stability, but they will continue to occur in every generation.

'03-0582' is a versatile Kentucky bluegrass variety, with applications on golf courses, sod farms, sports fields, home lawns, roadsides, cemeteries, and other turf areas, where bluegrass is well adapted. '03-0582' performs well in full sun or partial shade.

Example 3

Development and Characteristics of Kentucky Bluegrass Plant '03-0441'

'03-0441' Kentucky bluegrass, also known by the designation 'J-0441', originated as a low-growing, apomictic, single-plant selection from the progeny of Jacklin Seed breeding line '01-0307'. Breeding line '01-0307' was self pollinated to produce '03-0441'. Breeding line '01-0307' originated as the low-growing progeny of a hybrid field cross of Chicago II Kentucky bluegrass pollinated by breeding line '95-2986'. Breeding line '95-2986' had an excellent record in a 1997 turf trial in Idaho and a medium record in a 1999 trial in Maryland. It was first identified and harvested in the field in May 1995. Breeding line '95-2986' was a selection from the hybrid progeny of Midnight Kentucky bluegrass pollinated by Limousine, created as a paired field cross Jun. 3, 1991.

Seed harvested from '03-0441' was used to establish infrequently mowed trials in Idaho in 2006, and in Maryland and Ohio in 2007. '03-0441' was selected for release based on its turf quality performance in all months of the year under twice yearly mowing, as well as its seed production characteristics in Washington State.

'03-0441' is a classic low-growing plant with medium reproductive maturity, stocky culms and a dense proliferation of seed heads, featuring unexpected excellent powdery mildew disease resistance. Space plants average 35 cm across after one year's growth from rhizomes. Color of the stand at anthesis is light green with almost no purple coloration whatsoever. Plants are strongly blocky in shape with little to no lodging towards the perimeter of space plants. There is little to no influence of soil from plant to plant on productivity.

Panicles are small in size, however florets are large and panicle numbers are high. There is some tapering of culm length towards the perimeter of space plants giving the top of the space plant a rounded appearance. The center culms are approximately 10 cm taller than the culms at the perimeter of the plant. Culms are smooth to the touch in the upward direction and very lightly rough in the downward direction. Panicles are drooping at the tip and florets are drooping across most of the panicle but with the two lower nodes ascending. There is no waviness to the branching. Flag leaf margins are rough when felt in the downward direction and slightly rough in the upward direction. Flag leaf node is olive green in color and about 2 mm wide and slightly broader than the culm itself. Foliage color of space plants is medium dark green and flag leaves are distinctly bluish. Culms are medium green in color.

Progeny trials were conducted in spaced-plant nurseries, established June 2010, to determine the level of apomixis. A survey of 974 plants of showed that 12.8% of plants were variants in the vegetative (pre-flowering) stage, 1.4% were heading maturity variants, 0.1% were seedhead variants, 0.9% were variants appearing in the dry-down phase, and 2.1% were miniature plants. Many of the variants have shorter culms than the majority plant form with less purple panicle coloration. Variants may not be obvious in commercial seed production due to the masking effect of bulk populations. The spaced-plant apomixis rate of '03-0441' averages 83%, but it varies depending on growing conditions.

Variants are distributed across all phases of maturation. The primary variant has a more yellow panicle and lighter colored foliage than the majority plant form. About 1% of variants show a strongly drooping seed head with a longer panicle and lighter foliage. Most variants seem to share the stocky upright growth habit of the majority plant form.

'03-0441' Kentucky bluegrass is a stable and uniform variety. All seedlots evaluated have produced turf of comparable quality and acceptable uniformity. Aberrant progeny are rogued from Breeders, Foundation, and Registered fields to insure continued uniformity and stability, but they will continue to occur in every generation.

'03-0441' is a versatile Kentucky bluegrass variety, with applications on golf courses, sod farms, sports fields, home lawns, roadsides, cemeteries, and other turf areas, where bluegrass is well adapted. '03-0441' performs well in full sun or partial shade.

Example 4

Development and Characteristics of Kentucky Bluegrass Plant '99-2495'

'99-2495' Kentucky bluegrass, also known by the designation 'J-2495', originated as a low-growing, apomictic, single-plant selection from the progeny of Jacklin Seed breeding line '97-0429'. Breeding line '97-0429' was self pollinated to produce '99-2495'. Breeding line '97-0429' had a medium leaf color and reproductive maturity, a culm length of 54 cm, a high level of apomixis, and was susceptible to ergot and powdery mildew. Breeding line '97-0429' originated as a low-growing progeny of a hybrid cross of BlueChip Kentucky bluegrass pollinated by Blacksburg, created as a paired field cross Jun. 3, 1999.

Seed harvested from '99-2495' was used to establish infrequently mowed trials in Idaho in 2006, and in Maryland and Ohio in 2007. '99-2495' was selected for release based on its turf quality performance in all months of the year under twice yearly mowing, as well as its seed production characteristics in Washington State.

'99-2495' is a late maturing, shorter growing, fine textured version of a standard 5-Steps Above variety. '99-2495' has susceptibility to powdery mildew. Space plants average 45 cm across after one year's growth from rhizomes. The most unexpected and distinctive characteristic of this variety is its extremely fine, extremely dark green foliage as spaced plants. Of all the varieties in the Breeder blocks, this one has the most fine, dark leaves. Seed head productivity is excellent with some influence of plant-to-plant yield variation due to soil.

Panicle color at anthesis is light green with a diffusion of purplish color on the tips of florets. However, it does not appear as a distinct speckling as it does in some cultivars.

Culms are medium green in color and are mostly smooth with only a bit of roughness. Flag leafs are smooth when felt in the upward direction and rough in the downward direction. Attachment node of flag leaves is the same color as the culm with only a slight knob-like appearance, with little to no bend at the node. Spaced plant form is mostly blocky with a uniform culm length with little tapering (maybe 5 cm) towards the perimeter of the plant. Panicles are medium in size and florets are medium in size. Internode length gets shorter towards the tip of the panicle. There is a minor amount of waviness to the branching in the panicle, mostly towards the tip. Tips are mostly upright to slightly nodding. Most panicle branching is ascending however the lowest node is horizontal to descending. The attachment of the florets is horizontal to slightly downward.

Progeny trials were conducted in spaced-plant nurseries, established June 2010, to determine the level of apomixis. A survey of 1044 plants of '99-2495' showed that 11.7% of plants were variants in the vegetative (pre-flowering) stage, 1.8% were heading maturity variants, 0.2% were seedhead variants, 0.3% were variants appearing in the dry-down phase, and 0.8% were miniature plants. Many of the variants have shorter culms than the majority plant form with less purple panicle coloration. Variants may not be obvious in commercial seed production due to the masking effect of bulk populations. The spaced-plant apomixis rate of '99-2495' averages 85%, but it varies depending on growing conditions.

Variants in this cultivar appear during outbreaks of powdery mildew which shows resistant types. Most of the vegetative variants are slightly taller than the majority plant form. About 0.2% of plants are an open, easily lodged plant with drooping seed heads. The heading maturity variants differ from the majority plant form by a slightly taller and more yellow panicles.

'99-2495' Kentucky bluegrass is a stable and uniform variety. All seedlots evaluated have produced turf of comparable quality and acceptable uniformity. Aberrant progeny are rogued from Breeders, Foundation, and Registered fields to insure continued uniformity and stability, but they will continue to occur in every generation.

'99-2495' is a versatile Kentucky bluegrass variety, with applications on golf courses, sod farms, sports fields, home lawns, roadsides, cemeteries, and other turf areas, where bluegrass is well adapted. '99-2495' performs well in full sun or partial shade.

Example 5

Physiological and Morphological Characteristics of New Kentucky Bluegrass Varieties Table 1 shows a summary of the data obtained from trials held in 2010. The most promising varieties were planted into a spaced plant breeder blocks in Connell, Wash., in the heart of Kentucky bluegrass seed production country. The goal was to see how they performed in seed production, to pick the best of the best. After a year of observation and data collection, the three best entries were chosen; they appear at the top of Table 1. The remaining varieties in the table were not chosen due to one or more undesirable traits.

In Table 1 below, apomixis is the percentage of apomictic seed reproduction in the varieties. A value of 100 would indicate all offspring are identical genetically. Data in the remaining columns were visually rated on a 1 to 9 scale, with 9 equal to most low-growing characteristics, greatest powdery mildew resistance, highest seed yield, least soil variability from one plant to the next, and highest general turfgrass quality ratings in Ohio and Maryland averaged across monthly readings taken over three growing seasons. Mean values over 5 would be considered good and values of 8 or more could be considered outstanding. Commercial standards (i.e. varieties that are being sold on the market today) were tested in the initial Idaho studies. All commercial standards performed poorly compared to the promising experimentals of the present invention.

TABLE 1

| ID | Dwarf 28 Apr. 2011 | Dwarf 16 Jun. 2011 | Mildew 28 Apr. 2011 | Yield 16 Jun. 2011 | Soil var 9 = none | 2007 OH Rating 2008 | 2007 OH Rating 2009 | 2007 MD Rating 2008 | 2007 MD Rating 2009 | Apomixis |
|---|---|---|---|---|---|---|---|---|---|---|
| 03-0582 | 8 | 7 | 8 | 8 | 8 | 6.00 | 5.21 | 6.00 | 5.21 | 91 |
| 03-0441 | 8 | 6.5 | 9 | 7 | 6 | 6.00 | 6.57 | 6.67 | 4.00 | 83 |
| 99-2495 | 5.5 | 5.5 | 6 | 5.5 | 6 | 5.67 | 5.98 | 6.33 | 6.17 | 85 |
| 02-2139 | 6 | 7 | 2 | 4 | 5 | 6.33 | 6.33 | 6.67 | 4.50 | 91 |
| 02-2217 | 6 | 5 | 7 | 5 | 3 | 5.00 | 4.76 | 7.33 | 5.71 | 89 |
| 93-1436 | 6 | 3 | 7 | 8 | 8 | 4.33 | 6.50 | 7.33 | 5.17 | 87 |
| 93-1897 | 4 | 6 | 4 | 5 | 6 | 6.33 | 6.86 | 5.00 | 4.33 | 93 |
| 97-0428 | 6 | 6.5 | 4.5 | 6.5 | 5.5 | 5.00 | 6.55 | 6.00 | 5.50 | 91 |
| 99-2304 | 4 | 4 | 5 | 6 | 4 | 6.67 | 6.83 | | | 90 |
| 99-2891 | 6 | 7 | 7 | 6 | 7 | 4.67 | 5.61 | 6.67 | 5.67 | 95 |

As shown in Table 1, Kentucky bluegrass varieties designated '03-0582', '03-0441', and '99-2495' have the necessary attributes to provide a beautiful lawn with substantially reduced mowing requirements.

Example 6

Chlorophyll Concentration of New Kentucky Bluegrass Varieties

A Field Scout CM 1000™ chlorophyll meter was used for documenting the chlorophyll in field plots of infrequently mowed turf. In August 2009, 1000+ experimental plots were planted in Post Falls, Id. These plots were maintained under three-times-per-year mowing at 2.5-inch cut. Some plots did well under this mowing regime but most did not. A typical plot in the latter contained a majority of brown, lifeless stems and very little green leafy material. The chlorophyll meter picked up these differences in the good and bad plots and put a number to it.

This procedure is different than the lab procedure described elsewhere in that the CM 1000™ was detecting differences between the brown lifeless material and green leafy material in the plots maintained under infrequent mowing. In the lab procedure, only green tissue was used for chlorophyll concentration analysis. Moreover, the CM 1000™ did not produce chlorophyll readings in terms of parts per million of chlorophyll in leaf tissue. Instead, it produced a reading of 0 to 999 based on what the sensors detected in certain narrow wave bands (described below) which are sensitive to the spectral nature of the chlorophyll molecule. In the test plots, readings fell between 150 and 600 on that scale.

Visual turfgrass quality ratings and the CM 1000™ chlorophyll scans were reconciled as shown in FIG. 1. Forty-two readings were taken on the plots described above on Oct. 29, 2012 using both visual rating and CM 1000™ meter readings. These observations were graphed and were analyzed using linear regression. Solving the regression equation for a turf quality rating of '5' (the minimum acceptable number used in plant breeding to develop the cultivars) the equivalent CM 1000™ reading would be 341.7. The turfgrass plants of the present invention have a CM 1000™ meter reading of 341.7 and above on turfgrass mowed once every 4 weeks or fewer, combined with a previously specified chlorophyll concentration in green tissue—in other words, the ability to produce acceptable lawn turf while being mowed infrequently.

Regression analysis was performed to correlate the visual turfgrass quality ratings with Field Scout CM 1000™ scan results for test plots mowed three times per year in Idaho and the results are shown in FIG. 1. Regression analysis indicated that a visual quality estimate of 5 corresponds to a CM 1000™ meter reading of 341.7, with an unexpectedly high correlation co-efficient of 0.86, and an $R^2$ value of 0.73, which was significant at the 0.0001 level. In FIG. 1, circles represent individual observations, a solid line indicates regression fit to the data, and dashed lines indicate 95% confidence intervals.

Table 2 shows the chlorophyll concentration of Kentucky bluegrass varieties designated '03-0582', '03-0441', and '99-2495' compared to similar varieties; varieties that are under development are listed with their experimental numbers, while commercial varieties are shown with their cultivar names. Clippings were weighed (0.1 g) and placed in a glass test tube (1.0 cm in width and 14.8 cm in length) with 10 mL of dimethyl sulfoxide (DMSO) (Hiscox and Israelstam, 1979). Samples were incubated in 65° C. water for 1.5 hr. Upon completion, samples were passed through filter paper (Whatman 41, Whatman, England) and remaining extract (1 mL) transferred into cuvettes. Absorbance values were recorded at 663 nm and 645 nm wavelengths using a Spectrophotometer. Blanks were initially run and also after every sixth sample. The following formula was used to calculate total shoot chlorophyll: $(mg\ g^{-1}) = (8.02 * D_{663} + 20.2 * D_{645}) * 0.1$ (Arnon, 1949). Column 1 shows the sample name and column 2 shows the total shoot chlorophyll in mg/g.

TABLE 2

| Sample | Total Shoot Chlorophyll (mg/g) |
|---|---|
| 03-0582 | 2.57 |
| 99-2495 | 1.91 |
| 03-0441 | 3.21 |
| O2-2139 | 2.22 |
| O2-2217 | 2.61 |
| 93-1897 | 2.02 |
| 99-2304 | 2.42 |
| 97-0428 | 2.82 |
| 99-2891 | 3.46 |
| J-1770 | 2.35 |
| Troy | 1.18 |
| Camas | 1.40 |
| Nublue | 1.75 |
| Merit | 1.23 |
| Action | 0.89 |
| Thermal | 1.54 |

As shown in Table 2, bluegrass varieties designated '03-0582', '03-0441', and '99-2495' all have chlorophyll concentrations above 1.8 mg/g, whereas the commercial varieties Troy, Camas, Nublue, Merit, Action and Thermal all have chlorophyll concentrations below 1.8 mg/g.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the bluegrass varieties '03-0582', '03-0441' and '99-2495' developed by the method of the present invention disclosed above and recited in the appended claims has been made with the National Collections of Industrial, Food and Marine Bacteria (NCIMB), 23 St Machar Drive, Aberdeen, Scotland, AB24 3RY, United Kingdom. The date of deposit was Feb. 12, 2013. The deposit of 2,500 seeds was taken from the same deposit maintained by Jacklin Seed since prior to the filing date of this application. Upon allowance of any claims in this application, all restrictions on the availability to the public of the variety will be irrevocably removed by affording access to a deposit of at least 2,500 seeds of the same variety with the National Collections of Industrial, Food and Marine Bacteria (NCIMB), Aberdeen, Scotland, and the deposit is intended to meet all of the requirements of 37 C.F.R. 1.801-1.809. The NCIMB numbers are 42111, 42110, and 42112, respectively. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A bluegrass variety having desirable looking turf when mowed infrequently selected from the group consisting of bluegrass varieties '03-0582', '03-0441' and '99-2495', wherein representative samples of seed of said varieties were deposited under NCIMB Nos. 42111, 42110, and 42112, respectively.

2. The bluegrass variety of claim 1, further comprising at least one transgene.

3. A method for producing a bluegrass seed, comprising crossing two bluegrass plants and harvesting the resultant bluegrass seed, wherein at least one bluegrass plant is the bluegrass variety of claim 1.

4. An $F_1$ bluegrass seed produced by the method of claim 3.

5. An $F_1$ bluegrass plant, or a part thereof, produced by growing said seed of claim 4.

* * * * *